United States Patent [19]

Canales

[11] Patent Number: 5,418,616
[45] Date of Patent: May 23, 1995

[54] METHOD AND APPARATUS FOR OPTICALLY DETECTING THE DIMENSIONS OF AN OBJECT AND USE OF THE METHOD

[75] Inventor: Guillermo Canales, Barcelona, Spain

[73] Assignee: Zumbach Electronic AG, Orpund, Switzerland

[21] Appl. No.: 66,440

[22] Filed: May 25, 1993

[30] Foreign Application Priority Data

May 25, 1992 [CH] Switzerland .................. 01676/92

[51] Int. Cl.6 ........................................... G01N 21/00
[52] U.S. Cl. ................................. 356/439; 356/386; 356/384
[58] Field of Search ............... 356/386, 387, 438, 439, 356/384; 359/509

[56] References Cited

U.S. PATENT DOCUMENTS 4,647,199 3/1987 Ferber et al. .
4,787,750 11/1988 Nelson et al. ..................... 356/437

FOREIGN PATENT DOCUMENTS 1125197 3/1962 Germany .
3908533 9/1990 Germany .
4023610 1/1992 Germany .
4414388 4/1992 Japan .
2221296 1/1990 United Kingdom .

*Primary Examiner*—Richard A. Rosenberger
*Assistant Examiner*—Robert Kim
*Attorney, Agent, or Firm*—Spencer, Frank & Schneider

[57] ABSTRACT

Two optical windows serve for the passage of a light beam through a treatment chamber in which a product is disposed whose dimensions are to be detected. Between the treatment chamber and each one of the optical windows there is disposed a rotary valve, which permits the separation of the optical window from the treatment chamber. Thus it is possible to prevent a medium that adversely influences the optical windows in the treatment chamber from gaining access to the interior face of the windows if protection of the windows has priority over a measurement. It is thus possible to considerably extend the service life of the windows.

12 Claims, 2 Drawing Sheets

METHOD AND APPARATUS FOR OPTICALLY DETECTING THE DIMENSIONS OF AN OBJECT AND USE OF THE METHOD

CROSS REFERENCE TO RELATED APPLICATION

This application claims the priority of Application Ser. No. 01 676/92-6, filed May 25th, 1992, in Switzerland, the subject matter of which is incorporated herein by reference.

BACKGROUND OF THE INVENTION

The present invention relates to a method and to an apparatus for optically detecting the dimensions of an object in a chamber that is subjected to heavy soiling, wherein a light beam passes through windows of the chamber and the influence of the object on the light beam is detected. Generally, a light beam focused at the location of the object is periodically deflected in the direction of the dimension to be detected and a conclusion is drawn as to the dimension of the object from the duration for which the light beam is interrupted by the object. It is now clear that a precise measurement requires as unimpeded as possible a passage of the light beam through the windows of the chamber in which the object is disposed. However, this is no longer the case if the windows are highly soiled or even corroded. This is the case, in particular, in systems for extruding and subsequently vulcanizing certain products, for example, cables or wires that are encased in an insulation of cross-linkable plastics or rubber. In this process there is a particularly distinct danger of the windows becoming soiled by condensate and diverse residues, particularly during the vulcanization of rubber during which certain additives are separated. At the relatively high treatment temperatures in a range of 250° C., these impurities may actually be burnt in. Soiling may occur, in particular, also during the so-called flooding of the vulcanization tube before the vulcanization line is opened, that is, at the end of a production process. The disadvantageous consequences of condensate and soiling and the gradual corrosion of the interior faces of the windows have in the past been counteracted by heating the windows and flushing them with hot gases or superheated steam. Moreover, care has been taken that flooding always took place only to a level that lay below the windows which, however, resulted in a loss of finished product. In any case, it is unavoidable for the windows to have to be exchanged at relatively short intervals.

SUMMARY OF THE INVENTION

It is an object of the present invention to decisively improve the protection of the windows and to thus extend their service life as well as increase the reliability of the measurements. This is accomplished in that, during measuring pauses, shut-off members separate the windows from the chamber in which the object is disposed. In that way it is possible to prevent the windows from being unnecessarily soiled, particularly during the especially critical start-up phase and during flooding of the treatment chamber of a vulcanization system.

Preferably, known measures, such as heating the windows and flushing them with hot gas or superheated steam may be additionally employed. It is also possible to pressurize the chamber between a window and the closed shut-off member at a pressure which corresponds at least to the pressure existing in the treatment chamber so that, even if the shut-off members are not quite tight, no impurities from the treatment chamber can reach a window.

BRIEF DESCRIPTION OF THE DRAWINGS

The invention will now be described in greater detail with reference to an embodiment of the apparatus according to the invention and of its use according to the invention.

In the drawing figures.

DETAILED DESCRIPTION OF THE PREFERRED EMBODIMENT

Figure 1:
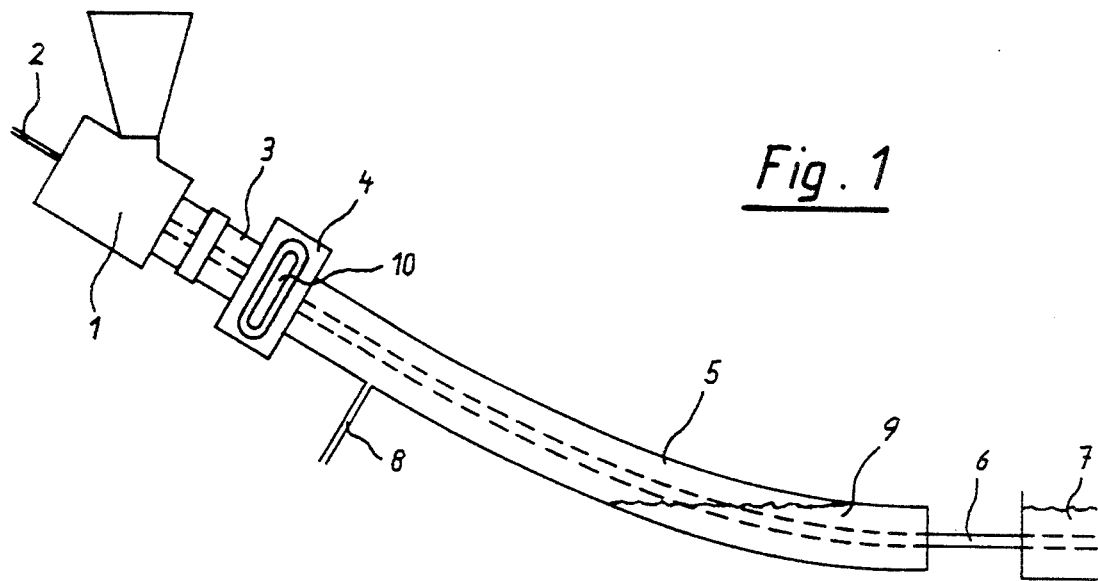
FIG. 1 is a schematic representation of an extruder and a connected vulcanization chamber.

FIG. 1 depicts schematically an extruder 1 which serves to encase a conductor or cable 2 in a cross-linkable plastic or a rubber. The encased product leaves extruder 1 through a telescoping tube 3 into a measuring unit 4 and from there into a vulcanization tube 5. The product 6 leaving the vulcanization tube travels into a water bath 7 where it is cooled. Through a conduit 8, steam or nitrogen is introduced into vulcanization tube 5 at a temperature around 250° C. and at a pressure up to 25 bar. As indicated in FIG. 1, a bath 9 of a molten salt may also be disposed in the vulcanization chamber.

FIG. 1 shows schematically an elongate measuring window 10 of measuring unit 4. This measuring unit has identical windows on facing sides so that a light beam is able to pass through these two windows in the manner mentioned above. This light beam permits the detection of the diameter of product 6 at the measuring location. In whichever way the vulcanization takes place, there exists a considerable danger of the interior of windows 10 becoming soiled which leads to the above-mentioned disadvantageous consequences.

Figure 2:
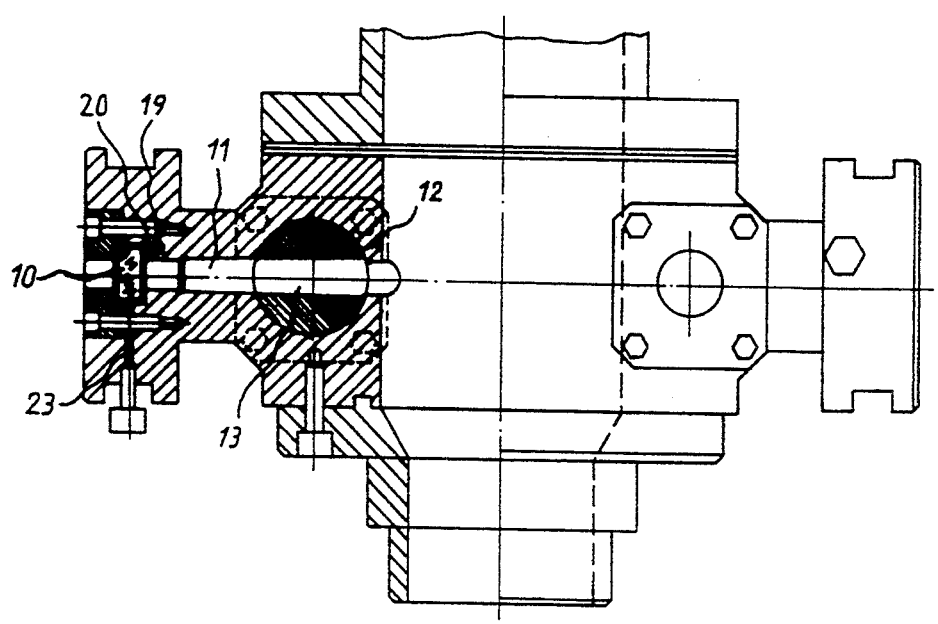
FIG. 2 is a top view, partially in section, of the measuring unit.
Figure 3:
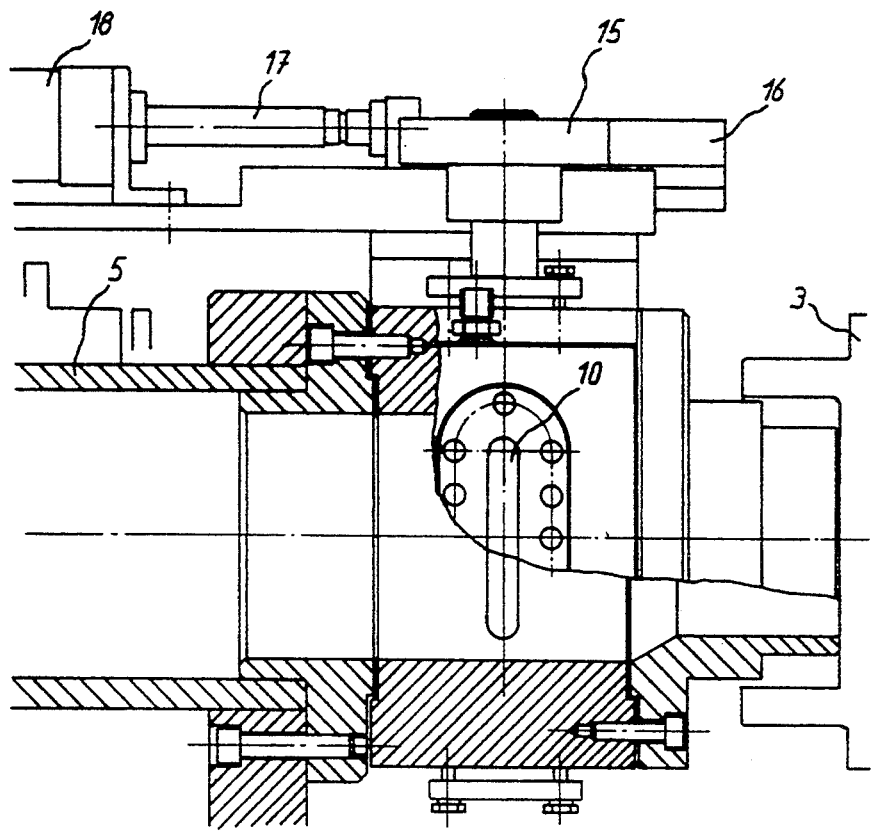
FIG. 3 is a side view, partially in section, of the measuring unit.
Figure 4:
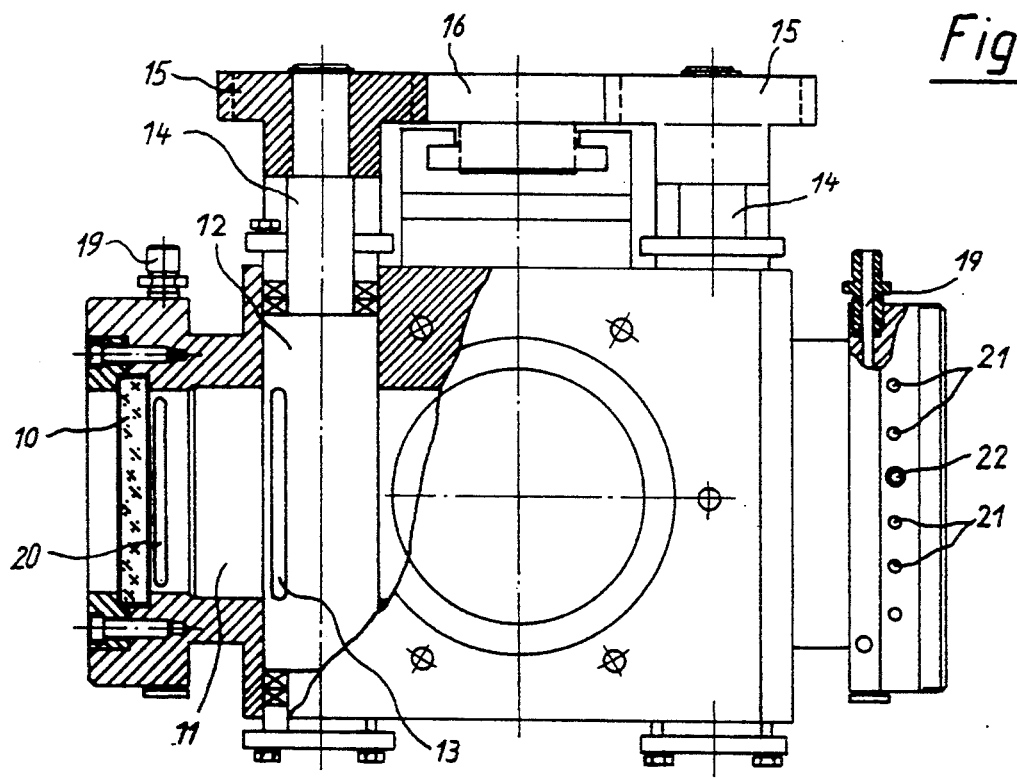
FIG. 4 is a front view, partially in section, of the measuring unit.

According to the invention, this problem is counteracted in that a shut-off member is disposed between each window 10 and the treatment chamber in tube 5. FIGS. 2 and 4 show one of the windows 10 in section. The window lies in a channel 11 leading to the treatment chamber of tube 5. In this channel, a rotary valve 12 is disposed which has a diametral passage 13 whose cross section corresponds to that of channel 11. FIG. 2 shows the rotary valve 12 in the open position, that is, its passage is flush with channel 11 so that the passage of a light beam through the window and the rotary valve into the treatment chamber is ensured. On the right side in FIGS. 2 and 4, the arrangement is symmetrical, that is, here again a rotary valve 12 is disposed within window 10 and the two rotary valves are opened and closed in synchronism, as will be described below. For this purpose, each rotary valve is provided with a pinion 15 on its upwardly extending shaft 14. This pinion meshes with a common toothed rod 16. According to FIG. 3, toothed rod 16 is connected with the piston rod 17 of an actuation cylinder 18, so that the mentioned synchronous operation of the two rotary valves for opening and closing the same is ensured. FIG. 2 shows an intake conduit 19 and a nozzle 20 through which a hot gas or superheated steam can be brought to the interior of window 10 in order to wash this window and avoid or remove possible condensate. In FIG. 4 it is indicated that bores 21 for accommodating heating elements to heat window 10 are disposed in the pipe ends accommodating windows 10. In another bore 22, there is a heat sensor 23 which controls the heating power regulating the temperature of window 10. Intake conduit 19 and nozzle 20 may simultaneously serve to put channel 11 between window 10 and the associated closed rotary valve 12 under a pressure which corresponds at least to the pressure in the vulcanization chamber, thus permitting neither gases nor liquid to pass from the vulcanization chamber to window 10.

During the particularly critical system start-up phase, rotary valves 12 are now closed so that no impurities reach the interiors of windows 10. Rotary valves 12 are opened again only after a certain delay so that the measurement of the product can begin. If production is interrupted, it is the custom that, if possible, the entire vulcanization chamber is flooded in order to cool the product therein. In this phase as well, rotary valves 12 are closed so that the entire vulcanization chamber can be flooded without adverse effects for windows 10. Although the use of the method according to the invention and of the apparatus according to the invention is of special interest for a vulcanization system according to FIG. 1, a corresponding procedure may of course be employed whenever the product to be measured is disposed in a chamber in which particularly critical conditions exist, at least temporarily, which would lead to soiling or even damage to the windows. Instead of rotatable valves, flat slides that can be pivoted or pushed into channel 11 could also be provided.

It would also be conceivable to provide a rotary valve 12 or, in particular, a flat shut-off slide of glass whose faces lying within channel 11 when the valve is closed, are practically self-cleaning due to the respective sliding movement, thus permitting measurements to be made when the valve is closed as well.

The additional shut-off member according to the invention offers the further advantage that, if a window is damaged or becomes untight, the associated shut-off member can be closed manually or automatically thus permitting the continuation to the end of a running process, however without measurements, or, if the shut-off member is transparent, with limited measuring accuracy. For example, a pressure sensor may be provided in the treatment chamber which closes the shut-off members if the pressure drops below a certain threshold.

Measuring windows 10 may also be provided at a different location, for example, in telescoping tube 3, as close to the extruder 1 as possible or further back in the treatment chamber.

It will be understood that the above description of the present invention is susceptible to various modifications, changes and adaptations, and the same are intended to be comprehended within the meaning and range of equivalents of the appended claims.

What is claimed is:

1. A method for optically detecting dimensions of an object in a chamber subjected to heavy soiling, comprising the steps of:
    passing a light beam through a window and into the chamber;
    measuring the influence of the object on the light beam to determine the dimensions of the object;
    providing a shut-off member having an opened and closed position between the window and the chamber; and
    separating the window from the chamber by closing the shut-off member during a pause in said measuring.

2. A method according to claim 1, further comprising the step of heating the window.

3. A method according to claim 2, wherein said heating step includes flushing the window with at least one of hot gas or superheated steam.

4. A method according to claim 1, further comprising the step of increasing a pressure between the window and the closed shut-off member to correspond at least to a pressure within the chamber.

5. A method according to claim 1, further comprising the step of closing the shut-off member when the window becomes damaged or loose.

6. A method according to claim 1, further comprising the step of automatically closing the shut-off member if an operating condition within the chamber becomes unacceptable.

7. An apparatus for optically detecting dimensions of an object in a chamber subjected to heavy soiling, comprising:
    two oppositely disposed windows each opening into the chamber through which a measuring light beam can be passed, whereby the influence of the object on the light beam is measurable to determine the dimensions of the object; and
    an actuatable shut-off member having an opened and closed position arranged between each said window and the chamber, said actuatable shut-off member being closable to separate the window from the chamber during a measuring pause in which the influence of the object on the light beam is not measured.

8. An apparatus according to claim 7, wherein said actuatable shut-off member comprises a rotary valve.

9. An apparatus according to claim 7, further comprising:
    a heater for heating a supply of at least one of hot gas and superheated steam; and
    an intake conduit and nozzle for supplying said windows with said at least one of hot gas and superheated steam.

10. An apparatus according to claim 6, further comprising a heating element for heating said windows.

11. An apparatus according to claim 6, wherein said actuatable shut-off member comprises a transparent material.

12. A method for optically detecting the dimensions of an extruded object in a vulcanization chamber subjected to heavy soiling, comprising the steps of:
    passing a light beam through a window and into the vulcanization chamber;
    detecting the influence of the extruded object on the light beam to determine the dimensions of the extruded object;
    providing a shut-off member having an opened and closed position between the window and the vulcanization chamber; and
    separating the window from the vulcanization chamber by closing the shut-off member during at least a start-up of a vulcanization process in the vulcanization chamber or flooding of the vulcanization chamber.

* * * * *